US010531816B2

(12) United States Patent
Ziemek et al.

(10) Patent No.: US 10,531,816 B2
(45) Date of Patent: Jan. 14, 2020

(54) EXPANDABLE PADDLE DISTRACTOR

(71) Applicant: Zimmer Biomet Spine, Inc., Broomfield, CO (US)

(72) Inventors: Terry Ziemek, Broomfield, CO (US); Susanne Duman, Boulder, CO (US); William Sandul, Broomfield, CO (US); Samuel Jebsen, Lafayette, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 228 days.

(21) Appl. No.: 15/421,827

(22) Filed: Feb. 1, 2017

(65) Prior Publication Data

US 2017/0215767 A1    Aug. 3, 2017

Related U.S. Application Data

(60) Provisional application No. 62/289,399, filed on Feb. 1, 2016.

(51) Int. Cl.
*A61B 5/107* (2006.01)
*A61B 17/02* (2006.01)
*A61B 90/00* (2016.01)

(52) U.S. Cl.
CPC ............ *A61B 5/1076* (2013.01); *A61B 17/02* (2013.01); *A61B 17/025* (2013.01); *A61B 2017/0256* (2013.01); *A61B 2090/061* (2016.02)

(58) Field of Classification Search
CPC ... A61B 5/1072; A61B 5/1076; A61B 17/025; A61B 17/0256
See application file for complete search history.

(56) References Cited

U.S. PATENT DOCUMENTS

| 5,599,279 | A | * | 2/1997 | Slotman | A61B 17/025 128/898 |
| 6,478,800 | B1 | * | 11/2002 | Fraser | A61F 2/4611 606/90 |
| 8,317,798 | B2 | * | 11/2012 | Lim | A61B 17/025 606/105 |
| 2004/0097951 | A1 | * | 5/2004 | Steffensmeier | A61B 5/107 606/102 |

(Continued)

*Primary Examiner* — Nicholas W Woodall
(74) *Attorney, Agent, or Firm* — Schwegman Lundberg & Woessner, P.A.

(57) ABSTRACT

Implementations described herein include surgical distraction devices having a distal movement assembly having a pusher plate comprising a first slot extending along a first axis disposed in a first side and a second slot extending along a second axis disposed in a second side thereof. The first axis is oriented at an angle of from about 60 to about 160 degrees from the second axis. The device further includes a first and second paddles, each paddle having a corresponding engagement mechanism for movably coupling the respective first or second paddle to the pusher plate when engaged in the respective slot. Rotational actuation of the proximal drive assembly causes proximal or distal movement of the pusher plate, causing the first and second engagement members to move relative to their respective slots, thereby moving the first paddle and the second paddle in opposing directions. Methods of using such surgical distraction devices to determine size of an intervertebral space are also described.

18 Claims, 20 Drawing Sheets

(56) References Cited

U.S. PATENT DOCUMENTS

| | | | | |
|---|---|---|---|---|
| 2007/0276370 A1* | 11/2007 | Altarac | ............... | A61B 17/0206 606/86 A |
| 2012/0185049 A1* | 7/2012 | Varela | ..................... | A61F 2/447 623/17.16 |
| 2014/0336767 A1* | 11/2014 | Keller | ................. | A61F 2/30771 623/17.16 |

* cited by examiner

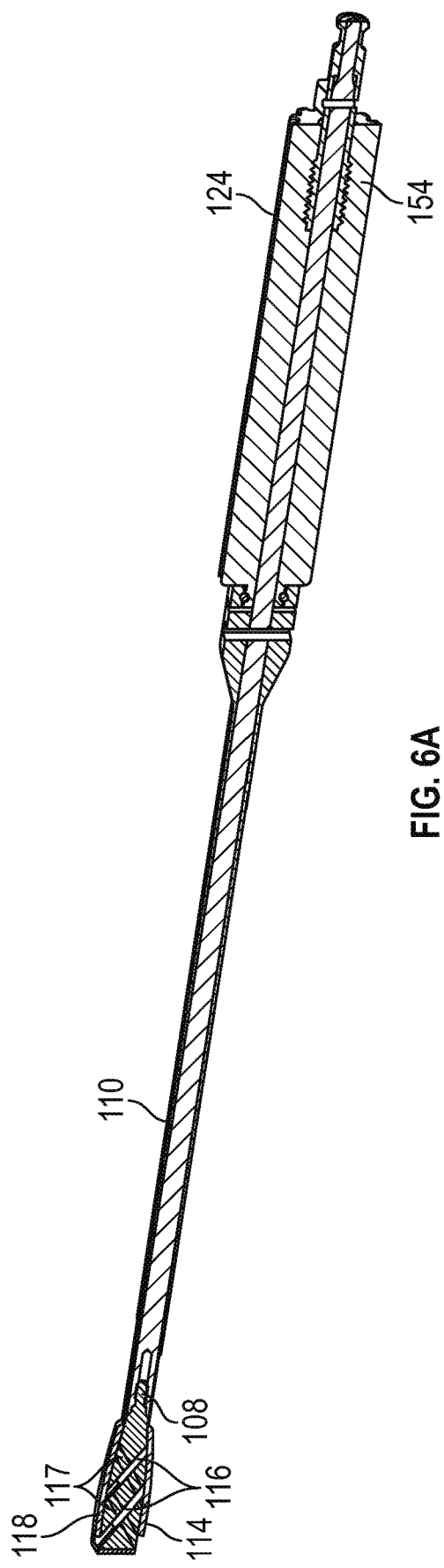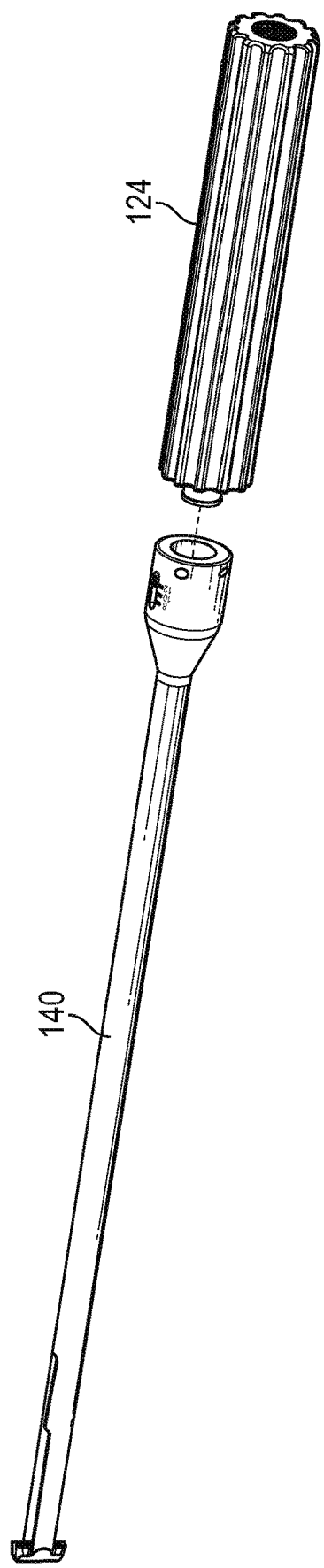
FIG. 6A
FIG. 6B

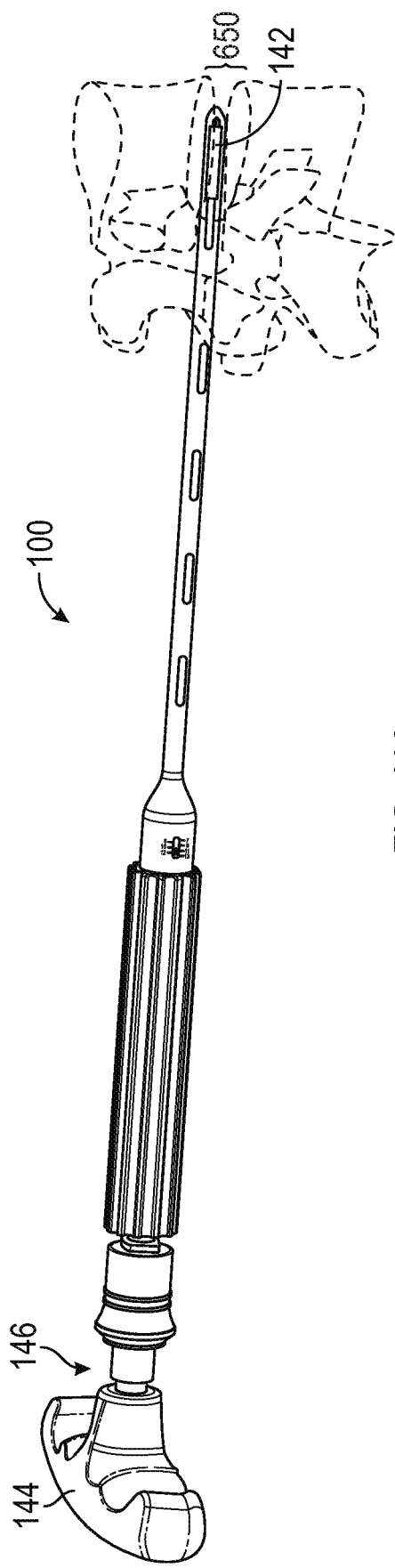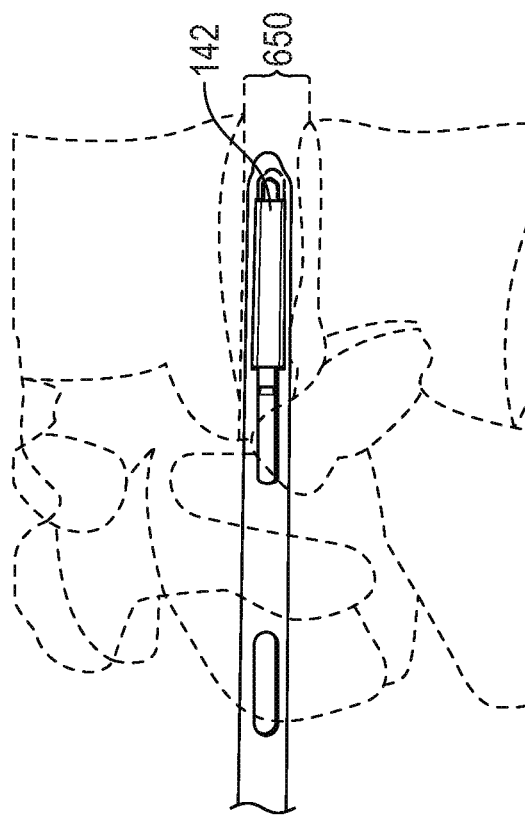
FIG. 11A
FIG. 11B

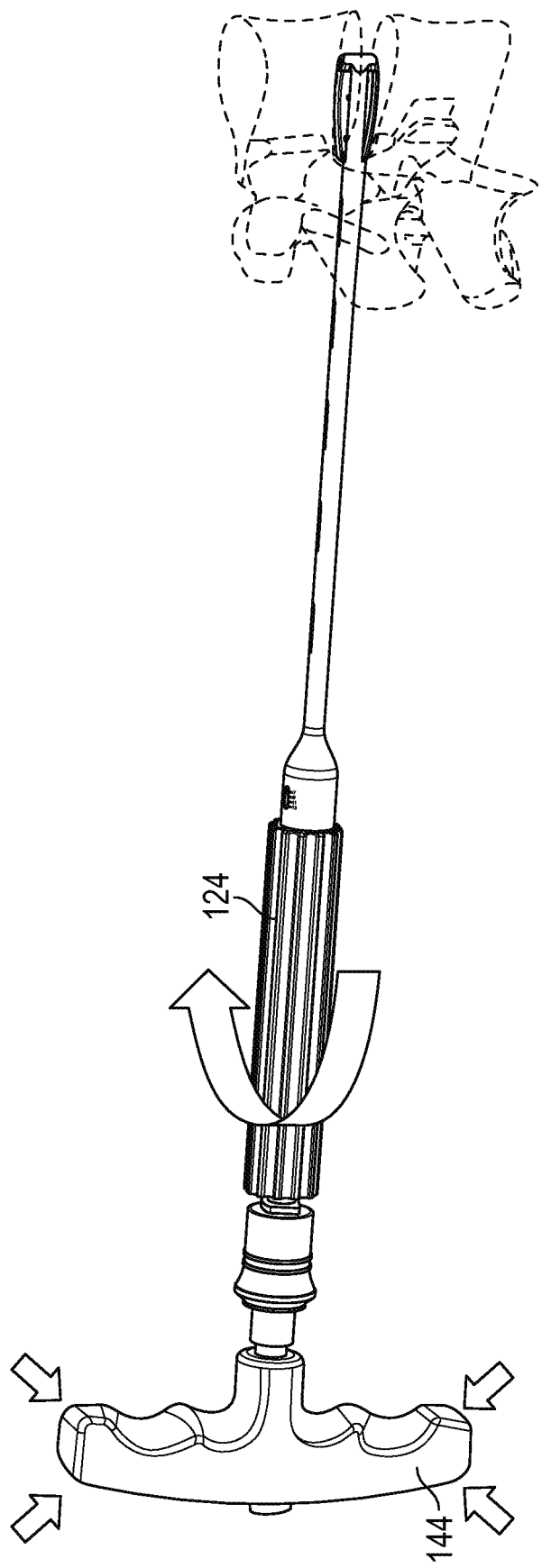
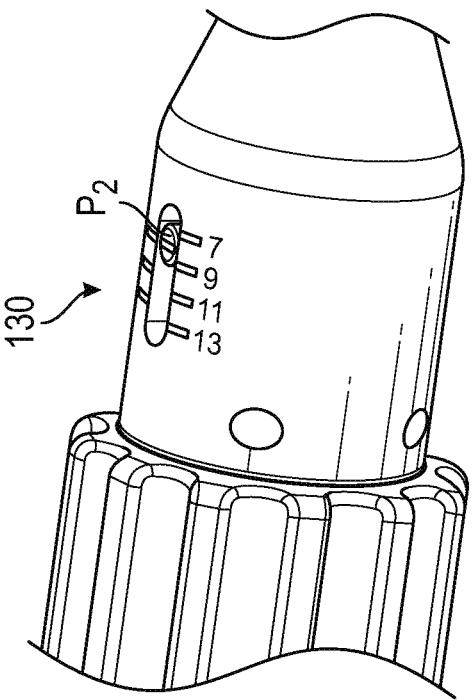
FIG. 12F
FIG. 12G

EXPANDABLE PADDLE DISTRACTOR

PRIORITY APPLICATION

This application claims the benefit of priority to U.S. Provisional Application Ser. No. 62/289,399, filed Feb. 1, 2016, the content of which is incorporated hereby by reference in its entirety.

FIELD

The present disclosure relates to expandable paddle distractors and associated systems and methods.

BACKGROUND

Spinal surgeries that require implantation of devices into intervertebral spaces are well known. In order to determine an appropriate size intervertebral implant, it may be necessary to use tools to measure the intervertebral space. Currently used tools may include tools that include snap-on heads of varying size that are switched out until the appropriate diameter across the intervertebral space is determined. Alternatively, a number of different tools, each of different size, may be used.

SUMMARY

The present inventors have recognized, among other things, that a problem to be solved can include the need for use of multiple differently-sized surgical distractors in order to make size determinations of intervertebral spaces. The present subject matter can help provide a solution to this problem, such as by providing a single expandable surgical distractor.

The surgical distractor of the present description can comprise a distal movement assembly comprising a pusher plate and a proximal drive assembly coupled to a proximal end of the pusher plate. The pusher plate can comprise a first slot disposed therein extending along a first axis and a second slot disposed therein extending along a second axis. The first slot can extend from a first side of the pusher plate towards an opposed second side of the pusher plate and the second slot can extend from a second side of the pusher plate towards the first side. The first axis can oriented at an angle of between about 60 degrees and about 160 degrees with respect to the second axis. The surgical distractor can further comprise a first paddle and a second paddle. The first paddle can comprise a first actuation plate and a first engagement plate substantially transverse to the first actuation plate. The first paddle can further comprise a first engagement member coupled to the first actuation plate for movably coupling the first paddle to the pusher plate when engaged with the first slot. The second paddle can comprise a second actuation plate and a second engagement plate substantially transverse to the second actuation plate. The second paddle can further comprise a second engagement member coupled to the second actuation plate for movably coupling the second paddle to the pusher plate when engaged with the second slot. Rotational activation of the proximal drive assembly can cause proximal or distal movement of the pusher plate, causing the first engagement member to move relative to the first slot and the second engagement member to move relative to the second slot, thereby moving the first paddle and the second paddle in opposing directions. Each of the opposing directions can be orthogonal to a longitudinal axis of the device.

The present description also provides for another method of determining the size of an intervertebral space. The method can comprise inserting a distal end of a distractor into an intervertebral space; attempting to turn the distal end of the distractor 90 degrees such that an axis through a greatest width of the distal end is aligned with the axis of the spine; engaging a proximal drive assembly of the distractor to move a pusher plate of the distractor along a longitudinal axis of the distractor, wherein engagement members disposed on each of the first and second paddle of the distractor engage with slots disposed in the pusher plate to cause the paddles to translate away from a longitudinal axis of the proximal drive assembly; and determining an implant size corresponding to the width of the distractor in the plane in which the first and second paddles are translated using an implant size indicator.

The present description further provides for method of determining the size of an intervertebral space. The method can comprise inserting a distal end of a distractor into an intervertebral space; attempting to turn the distal end of the distractor 90 degrees such that an axis through a greatest width of the distal end is aligned with the axis of the spine; returning the distractor to its original orientation; engaging a proximal drive assembly of the distractor to move a pusher plate of the distractor along a longitudinal axis of the distractor, wherein engagement members disposed on each of the first and second paddle of the distractor engage with slots disposed in the pusher plate to cause the paddles to translate away from a longitudinal axis of the proximal drive assembly; attempting, an additional time, to turn the distal end of the distractor 90 degrees such that an axis through a greatest width of the distal end is aligned with the axis of the spine; and repeating the method until the maximum diameter of the distal end of the distractor that is capable of fitting snugly within the intervertebral space in an upright configuration is determined.

This overview is intended to provide an overview of subject matter of the present patent application. It is not intended to provide an exclusive or exhaustive explanation of the invention. The detailed description is included to provide further information about the present patent application.

DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6A provides a cross-sectional view of internal portions of an exemplary pusher plate according to the present description.

FIG. 6B provides perspective views of external portions of an exemplary pusher plate according to the present description.

FIGS. 11A-11I provide various illustrations of an exemplary surgical distraction device and intervertebral space during one possible method of use.

FIGS. 12A-12J provide various illustrations of an exemplary surgical distraction device and intervertebral space during one possible method of use.

DETAILED DESCRIPTION

The present description relates to a surgical distraction device that allows for more efficient sizing of intervertebral spaces. As noted above, presently used devices for measuring intervertebral spaces suffer the drawback of the requirement of removing the device from the space entirely in order to replace with a larger or smaller sized head, or substituting in an entirely different device. The present description provides for a device that can be expanded to varying sizes until the intervertebral space (and corresponding implant size determination) is made, without removing the device entirely from the space.

Figure 1:
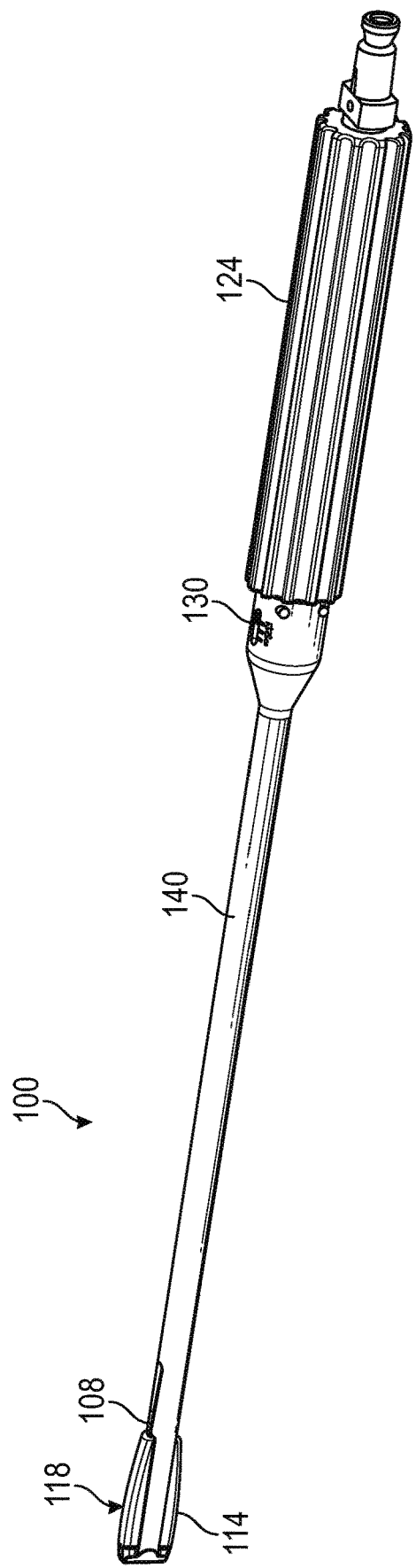
FIG. 1 provides a perspective view of an exemplary surgical distraction device according to the present description.

FIG. 1 provides a perspective view of an exemplary surgical distraction device 100 according to the present description. In general, the surgical distraction device can comprise a first paddle 114 and a second paddle 118 that are slidably coupled to a pusher plate 108 (shown in FIGS. 2A-2B) such that proximal and distal movement of the pusher plate causes the first and second paddles 114, 118 to move in opposing directions that are substantially transverse to the longitudinal axis of the device 100. The pusher plate 108 can be rotationally actuated by a proximal drive assembly 110 that is coupled to a proximal end of the pusher plate 108 (shown in FIGS. 2A-2B). A turning nut 124 can be coupled to the proximal drive assembly 110 and manipulation of the turning nut 124 can actuate the proximal drive assembly 110. The device 100 can further comprise an indicator 130 that displays the size of the intervertebral implant that corresponds to a given distance between an outer side 132 of the first paddle 114 and the outer side 132 of the second paddle 118. The device can also comprise a housing 140 that can be configured to surround the proximal drive assembly 110. These features will each be described more particularly in the following description.

Figure 2A:
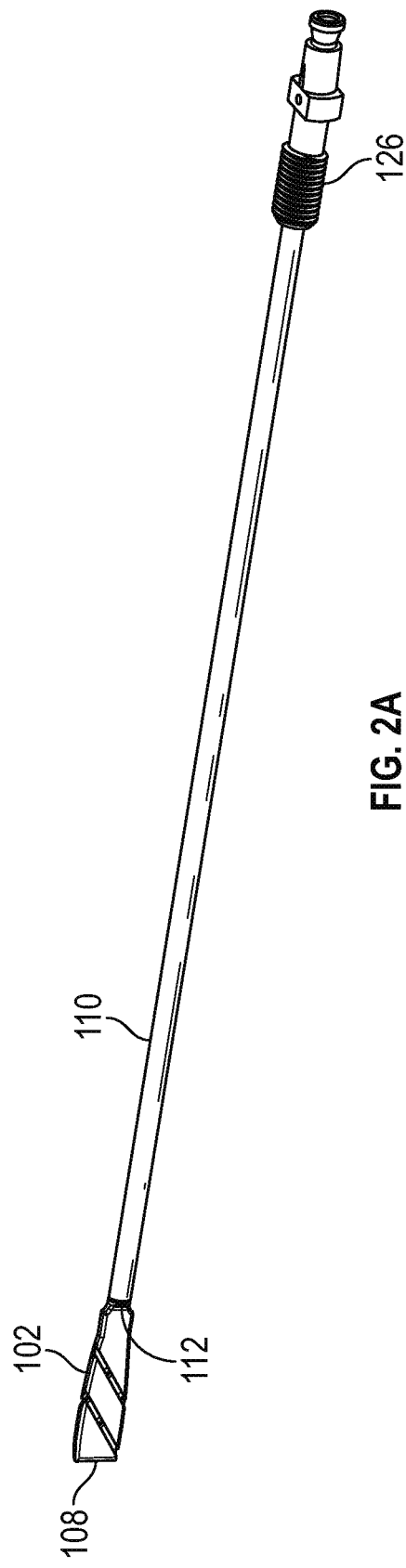
FIG. 2A provides a perspective view of internal components of an exemplary surgical distraction device according to the present description.
Figure 2B:
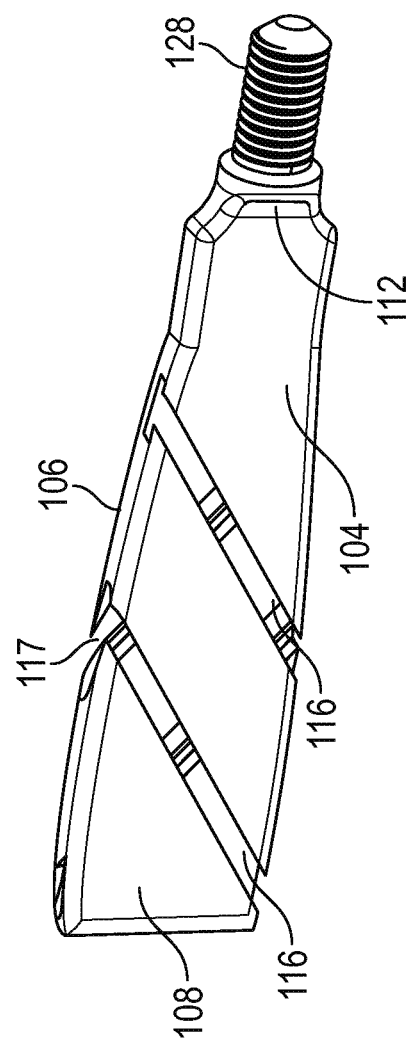
FIG. 2B provides a perspective view of an exemplary pusher plate according to the present description.

As further illustrated in FIGS. 2A-2B, the surgical distraction device 100 can comprise a distal movement assembly 102 at the distal end thereof that is movably coupled to a first paddle 114 and a second paddle 118. Distal movement assembly 102 can comprise a pusher plate 108 and a proximal drive assembly 110 coupled to a proximal end of the pusher plate 108. The pusher plate 108 can comprise a first slot 116 disposed therein an extending along a first axis and a second slot 117 disposed therein extending along a second axis. The first slot 116 can extend from a first side 104 of the pusher plate 108 towards a second side 106 of the pusher plate 108 and the second slot 117 can extend from a second side 106 of the pusher plate 108 towards the first side 104. The first and second slots 116, 117 can extend partially through or completely through the pusher plate 108. In at least one example, the pusher plate 108 can comprise a threaded coupling portion 128 (see, e.g., FIG. 2B) near distal end 112 that can be mateable with internal threads of the proximal drive assembly 110 in order to secure the proximal drive assembly 110 to the pusher plate 108.

As further illustrated in FIGS. 3A-4B, the distraction device 100 can further comprise a first paddle 114 and a second paddle 118. The first paddle 114 and the second paddle 118 can each comprise, respectively, a first engagement member 120 and a second engagement member 122. The distal movement assembly 102 can be actuated to move the first paddle 114 and the second paddle 118 towards or away from each other as described in further detail below.

Figure 3A:
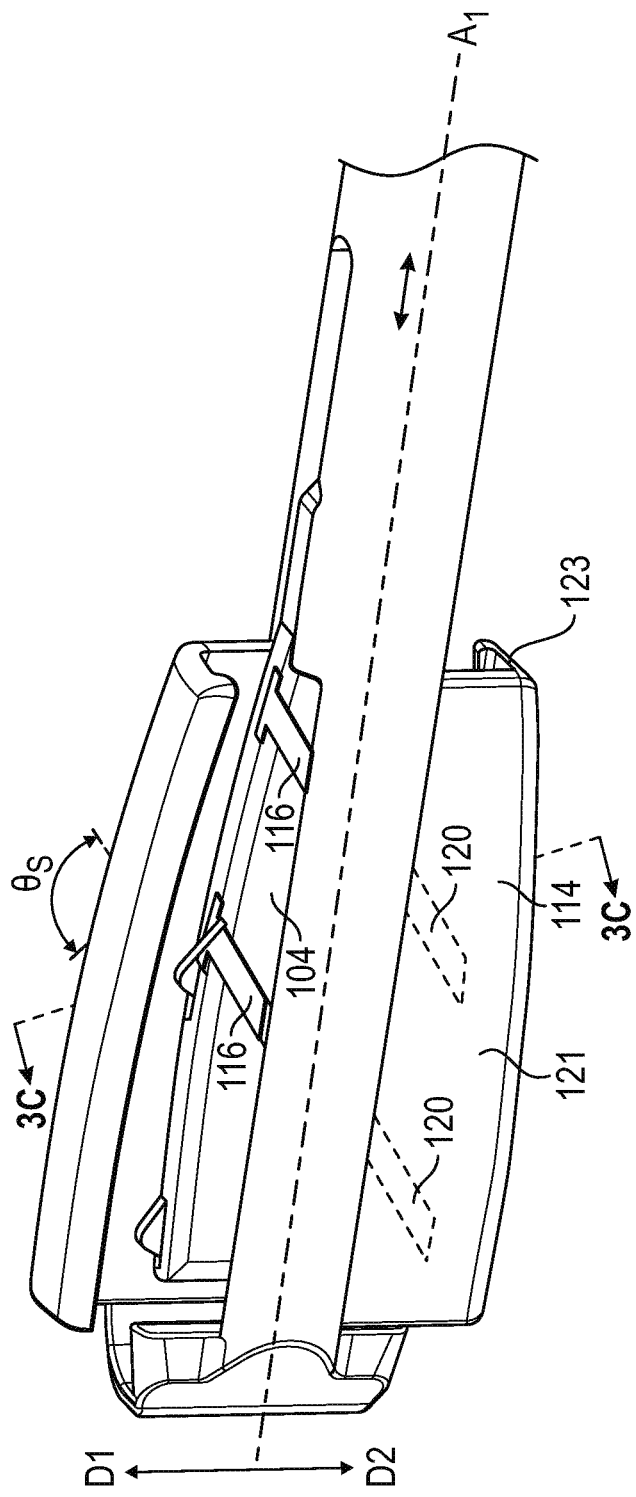
FIG. 3A provides a perspective view of a distal end of one exemplary surgical distraction device according to the present description.
Figure 3B:
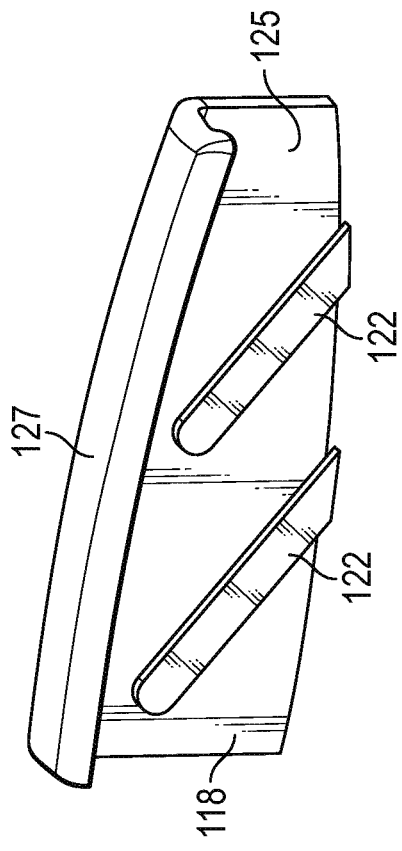
FIG. 3B provides a close up view of one exemplary paddle according to the present description.
Figure 3C:
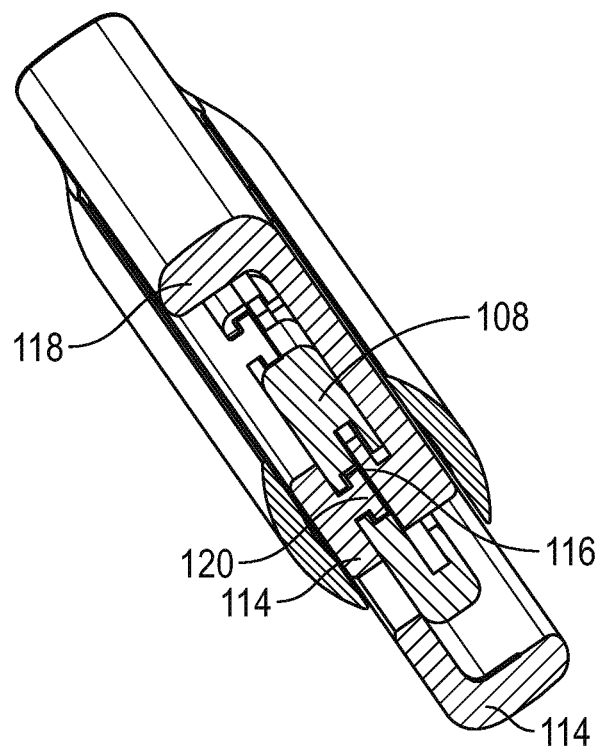
FIG. 3C provides a cross sectional view corresponding to section line 3C in FIG. 3A.

In one example illustrated in FIGS. 3A-3C, the surgical distraction device 100 can comprise a first paddle 114 and a second paddle 118. The first paddle 114 can comprise a first actuation plate 121 and a first engagement plate 123 that can be substantially transverse to the first actuation plate 121. The first paddle 114 can further comprise a first engagement member 120 coupled to and extending from the first actuation plate 121 for movably coupling the first paddle 114 to the pusher plate 108. Likewise, the second paddle 118 can comprise a second actuation plate 125 and a second engagement plate 127 that can be substantially transverse to the first actuation plate 125. The second paddle 118 can further comprise a second engagement member 122 coupled to and extending from the second actuation plate 125 for movably coupling the second paddle 118 to the pusher plate 108. Accordingly, the paddles 114, 118 engage the pusher plate 108 via engagement members (such as 120, 122) disposed on actuation plates (such as 121, 125) sliding within slots (such as 116, 117). The first engagement member 120 can comprise a first rail for engaging the first slot 116 on the first side 104 of the pusher plate 108 and the second engagement member 122 can comprise a second rail for engaging the second slot 117 on the second side 106 of the pusher plate 108. The first engagement member 120 and the first slot 116 and the second engagement member 122 and the second slot 117 can be matingly keyed as best illustrated in FIG. 3C. The first slot 116 of the pusher plate 108 can comprise a plurality of first slots 116 and the first engagement member 120 can comprise a corresponding plurality of first engagement members 120. Likewise, the second slot 117 of the pusher plate 108 can comprise a plurality of second slots 117 and the second engagement member 122 can comprise a corresponding plurality of second engagement members 122.

Figure 4A:
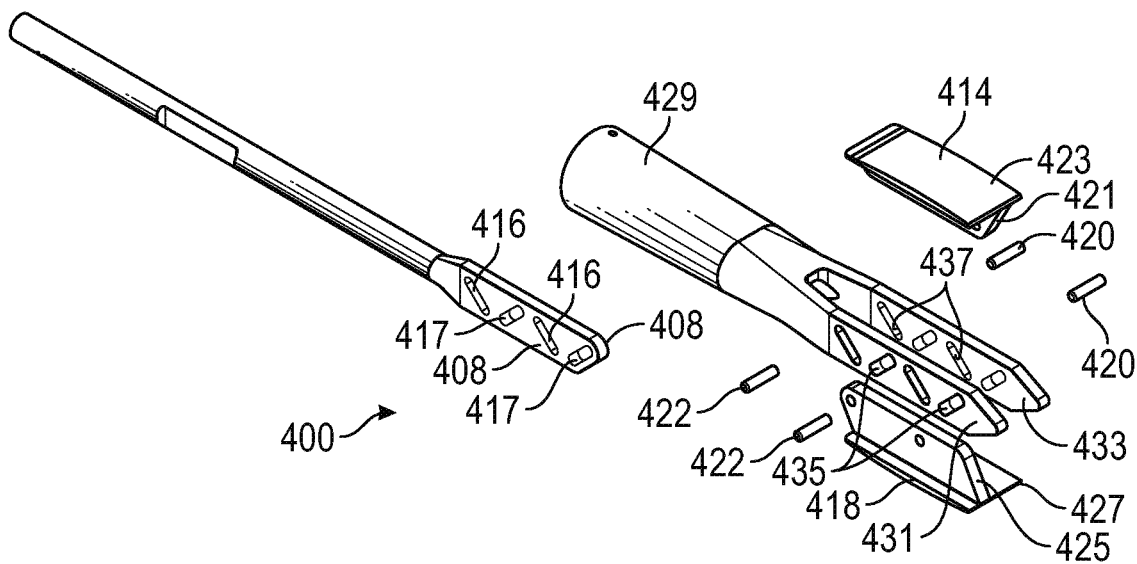
FIG. 4A provides an exploded perspective view of a distal end of one exemplary surgical distraction device according to the present description.
Figure 4B:
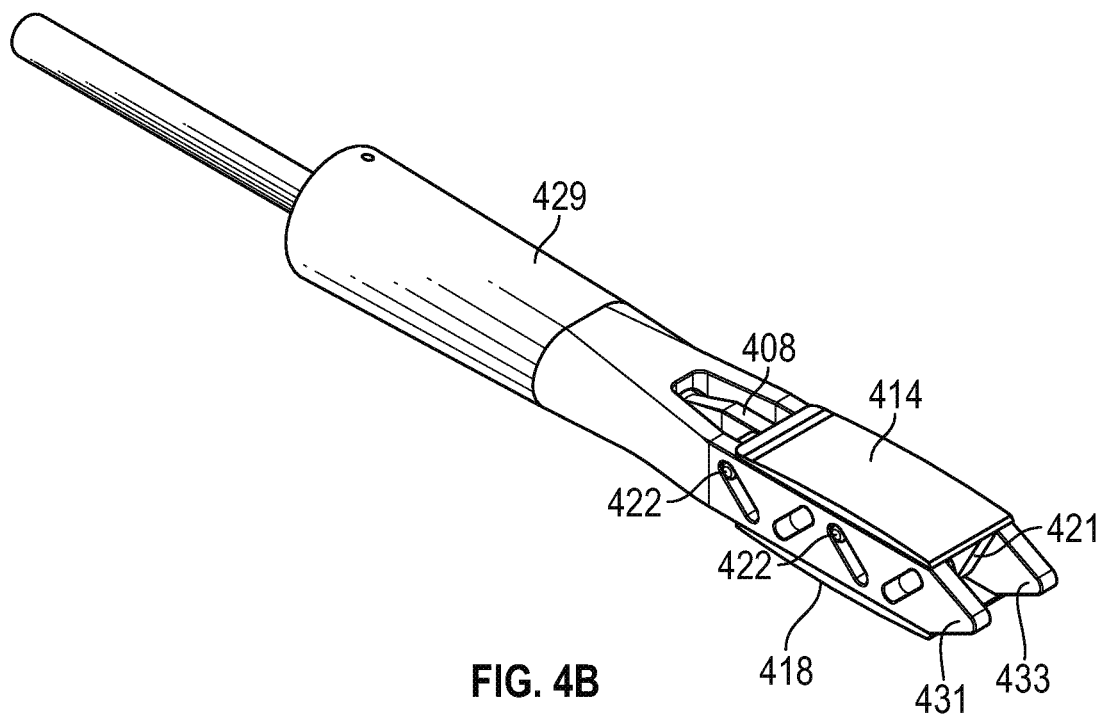
FIG. 4B provides an assembled perspective view of the distal end of the surgical distractor of FIG. 4A according to the present description.

In another example illustrated in FIGS. 4A-4B, the surgical distraction device 400 can comprise a first paddle 414 and a second paddle 418. The first paddle 414 can comprise a first actuation plate 421 and a first engagement plate 423 that can be substantially transverse to the first actuation plate 421. The first paddle 414 can further comprise a first engagement member 420 coupled to the first actuation plate 421 for movably coupling the first paddle 414 to the pusher plate 408. Likewise, the second paddle 418 can comprise a second actuation plate 425 and a second engagement plate 427 that can be substantially transverse to the first actuation plate 425. The second paddle 418 can further comprise a second engagement member 422 coupled to the second actuation plate 425 for movably coupling the second paddle 418 to the pusher plate 408. Accordingly, as with the example described above, the paddles 414, 418 engage the pusher plate 408 via engagement members (such as 420, 422) disposed on actuation plates (such as 421, 425) sliding within slots (such as 416, 417). The first engagement member 420 can comprise a first pin coupled to and extending from the first actuation plate 421 for engaging the first slot 416 of the pusher plate 408 and the second engagement member 422 can comprise a second pin coupled to and extending from the second actuation plate 425 for engaging the second slot 417 on the second side 406 of the pusher plate 408. The first slot 416 of the pusher plate 408 can comprise a plurality of first slots 416 and the first engagement member 420 can comprise a corresponding plurality of first engagement members 420. Likewise, the second slot 417 of the pusher plate 408 can comprise a plurality of second slots 417 and the second engagement member 422 can comprise a corresponding plurality of second engagement members 422. In another example, the surgical distraction device can further comprise a support member 429 having a first support 431 and a second support 432 spaced from the first support. The support member 429 can be positioned such that the first actuation plate 423 is substantially parallel to and in between the first support 431 and the pusher plate 408 and that the second actuation plate 427 is substantially parallel to and in between the second support 433 and the pusher plate 408. The first and second supports 431, 433 can have slots 435, 437 disposed therein that correspond to at least one of the first and second slots (or plurality of slots) 416, 417 disposed in the pusher plate 408. The support member 429 can provide further support for the first and second paddles 414, 418 as they translate or can be configured to facilitate relative movement between the first and second paddles 414, 418.

In each of the examples described above, the first and second engagement plates (such as 123, 127, 423, 427) can provide surface area to abut anatomical structure during use of the distraction device (such as 100, 400). Additionally, the edges of the first and second engagement plates (such as 123, 127, 423, 427) that abut the first and second actuation plates (such as 121, 125, 421, 425) can optionally be chamfered or rounded (not specifically identified in the illustrations) to smooth transitions between the various surfaces and ease the ability to manipulate the surgical distraction device (such as 100, 400) during use.

In each of the examples described above, rotational actuation of the proximal drive assembly (such as 110, 410) causes proximal or distal movement of the pusher plate (such as 108, 408) engaging the first and second engagement members (such as 120, 122, 420, 422). Proximal/distal movement of the proximal drive assembly (such as 110, 410) can move the first and second engagement members (such as 120, 122, 420, 422) within the corresponding slots (such as 116, 117, 416, 417), thereby moving the first paddle (such as 114, 414) and the second paddle (such as 118, 418) in opposing directions (D1 and D2). The opposing directions can be orthogonal to longitudinal axis $A_1$ of the surgical distraction device and proximal drive assembly. The rotation of the proximal drive assembly (such as 110, 410) can occur within (and is generally hidden by) turning nut 124, which surrounds at least a portion of the proximal drive assembly.

In each of the examples described above, the plurality of first slots (such as 116, 416) on the first slotted surface (such as 104, 404) can be positioned parallel to one another and the plurality of second slots (such as 117, 417) on the second slotted surface (such as 106, 406) can be positioned parallel to one another. The first slots (such as 116, 416) on the first slotted surface (such as 104, 404) can be generally oriented with respect to the second slots (such as 117, 417) on the second slotted surface (such as 106, 406) at an angle θs. In some examples, θs can be an angle between about 60 degrees and about 160 degrees, more particularly, θs can be a value between about 75 degrees and about 105 degrees, and, most particularly, θs can be a value between 80 degrees and 100 degrees.

Returning to FIG. 1, in at least one example, the surgical distraction device can comprise a turning nut 124 that is coupled to the proximal drive assembly 110. In such an example, manipulating the turning nut 124 can result in advancing or retracting of the pusher plate 108, and thus movement of the first and second paddles 114 and 118. For example, in the illustrated exemplary embodiment of FIGS. 3A-3C, retracting the pusher plate 108 with the distal movement assembly 102 can cause the first paddle 114 and second paddle 118 to expand outward from the pusher plate 108 and advancing the pusher plate 108 can cause the first paddle 114 and second paddle 118 to contract toward the pusher plate 108. The turning nut 124 may be threadably engaged with the proximal drive assembly 110 and the proximal end of the surgical distraction device 100, e.g., at threaded engagement portion 126 (see FIG. 2A).

Figure 5:
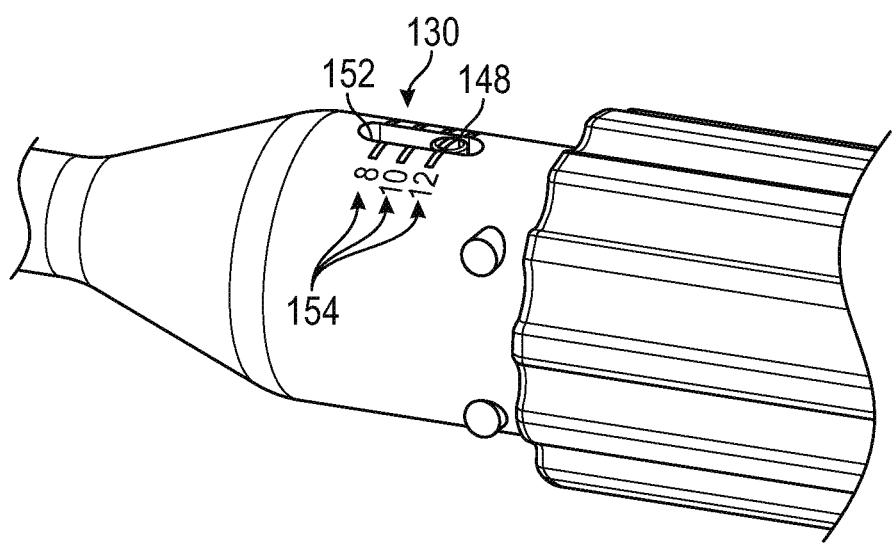
FIG. 5 provides a close up perspective view of an indicator on an exemplary surgical distraction device according to the present description.

As further illustrated in FIG. 5, the surgical distraction devices 100 of the present description can further comprise an indicator 130 that displays the size of intervertebral implant that corresponds to a given distance from an outer side 132 of the first paddle 114 to an outer side 132 of the second paddle 118. The indicator 130 can be positioned proximate the turning nut 124. The indicator 130 may comprise an indicator pin 148 that translates along a slot 152 as the paddles 114, 118 expand and contract. In an example, the indicator pin 148 is coupled to a portion of the proximal drive assembly 110, which translates relative to housing 140. The indicator pin 148 can display the intervertebral implant size according to size markings 154 positioned along the edge of the slot 152 that correspond to the distance from an outer surface of the first engagement plate 123 to the outer surface of the second engagement plate 127. In one example, the size markings 154 are calibrated to reflect the distraction distance based on the translation of the indicator 130 caused by movement of the proximal drive assembly 110.

Figure 6C:
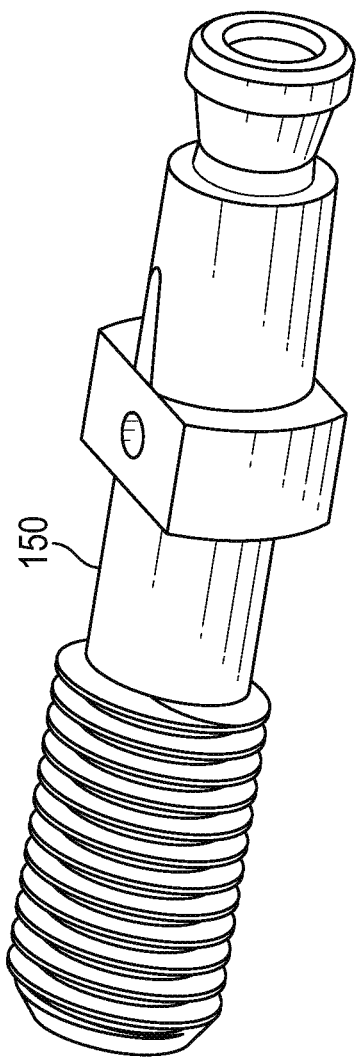
FIG. 6C provides a perspective view of a threaded connector.
Figure 6D:
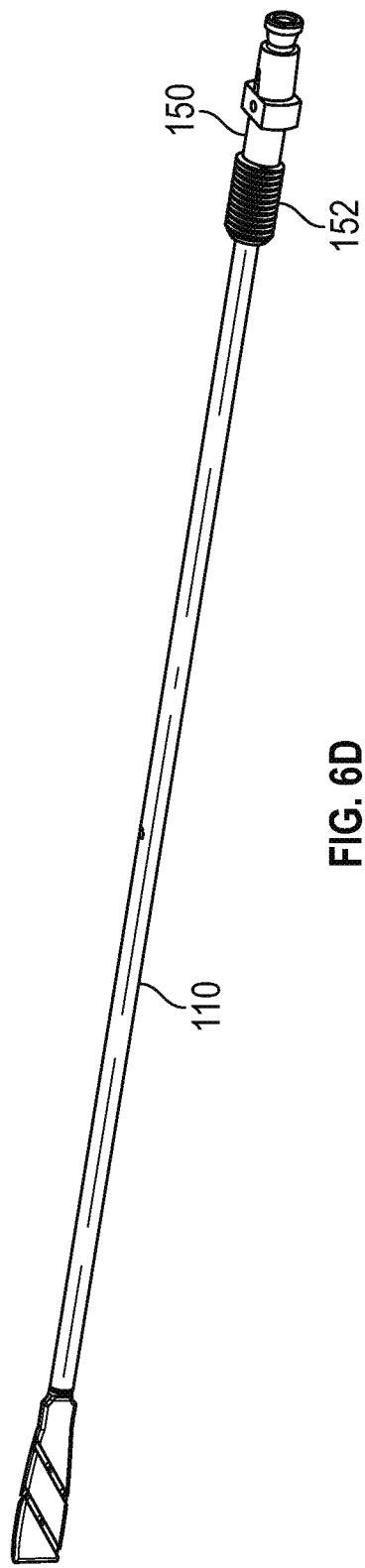
FIG. 6D provides a perspective view of portions of an exemplary surgical distraction device according to the present description.

FIG. 6A illustrates a cross-sectional view of a number of the components of the surgical distraction device, including the pusher plate 108, proximal drive assembly 110, and turning nut 124. As illustrated in FIG. 6B, the surgical distraction devices 100 can further comprise a housing 140. The housing 140 can be configured to surround the proximal drive assembly 110 (though shown separately in FIG. 6B). The fully assembled distraction device 100 with housing surrounding proximal drive assembly 110 is shown in FIG. 1. The housing 140 can surround the proximal drive assembly 110 and also partially surround the pusher plate 108, the first paddle 114, and the second paddle 118. The turning nut 124 can also at least partially surround the proximal drive assembly 110. The turning nut 124 can be coupled to the proximal drive assembly 110 via a threaded quick connect device 150, shown in FIG. 6C. As illustrated in FIG. 6D, the threaded quick connect device 150 can be mechanically coupled to the proximal drive assembly 110. The threaded quick connect device 150 can comprise external threads 152 that can be capable of engaging internal threads of the turning nut 124 at a rear portion of the turning nut 154 (see FIG. 6A) thus enabling manipulation of the turning nut 124 to actuate the proximal drive assembly 110.

Figure 7A:
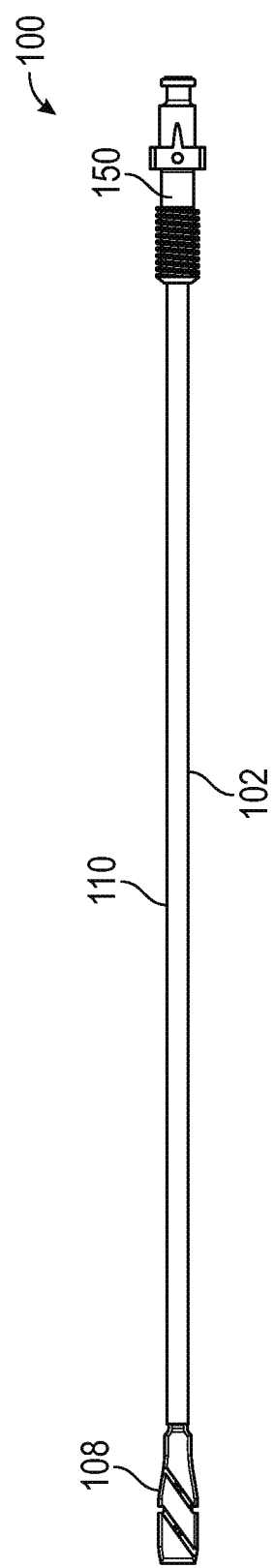
FIG. 7A provides a cross-sectional view of portions of an exemplary surgical distraction device according to the present description.
Figure 7B:
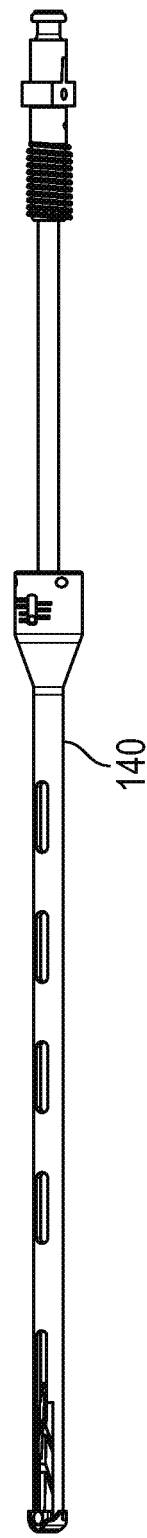
FIGS. 7B-7D provide close up cross-sectional views of the portions of the surgical distraction device of FIG. 7A.
Figure 7C:
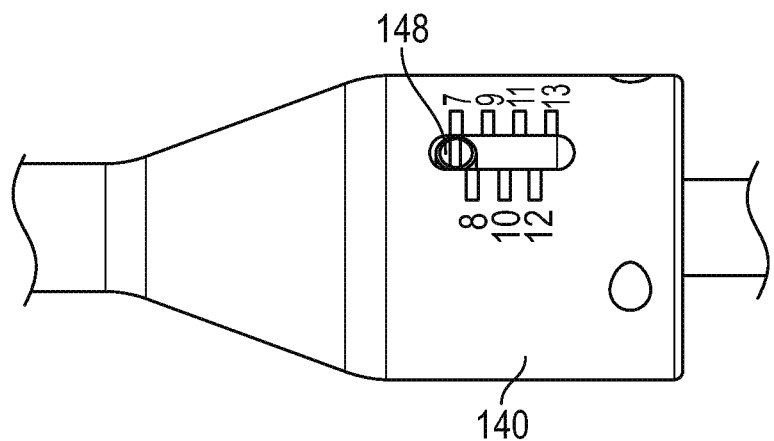
Figure 7D:
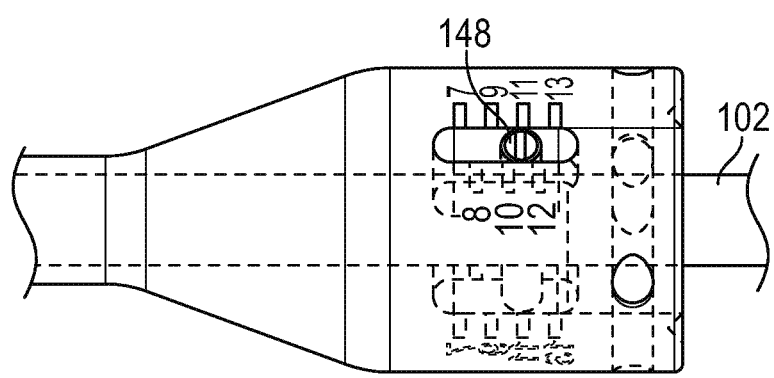
Figure 8:
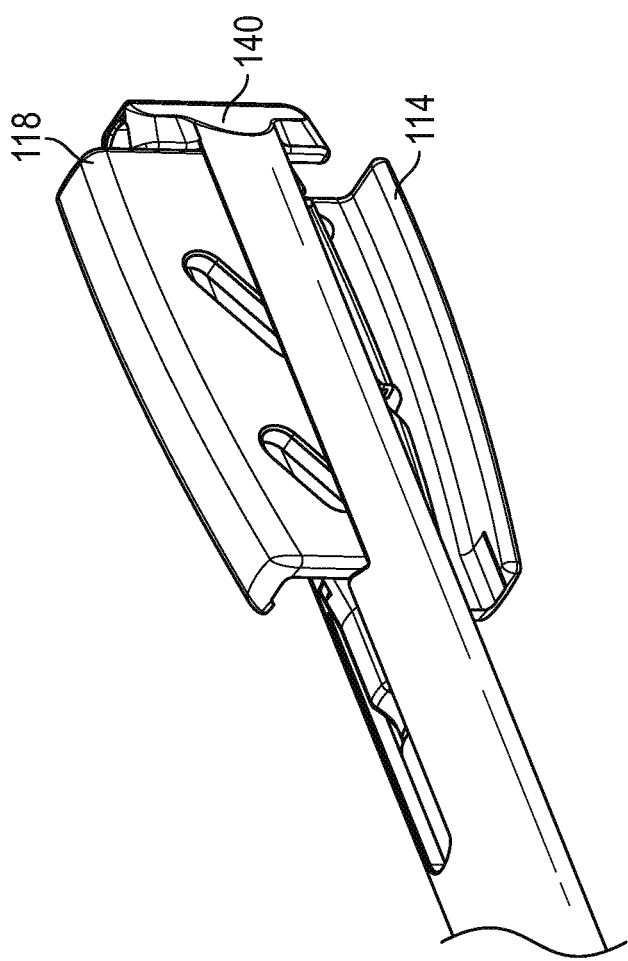
FIG. 8 provides a perspective view of exemplary paddles in relation to the housing surrounding said paddles.

This concept can be further understood by references to FIGS. 7A to 7D. FIGS. 7A and 7B provides cross-sectional views of a surgical distraction device 100 shown without turning nut 124 present. The proximal drive assembly 110, pusher plate 108, and quick connect device 150 can cooperatively form the distal movement assembly 102. The housing 140 can be coupled to the distal movement assembly 102 via the indicator pin 148 (shown in FIGS. 7C and 7D). This can prevent rotation of the housing 140 relative to the distal movement assembly 102 but can allow for some movement along the longitudinal axis $A_1$ (illustrated in FIG. 3A) of the proximal drive assembly 110. Translation of the housing 140 relative to the proximal drive assembly 110 causes the two paddles 114, 118 to distract/contract.

Figure 9:
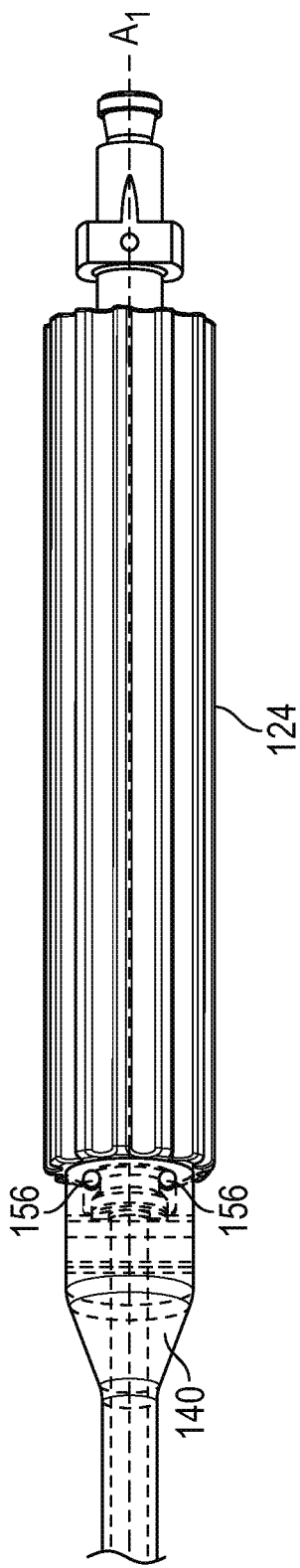
FIG. 9 provides a side view of an exemplary turning nut according to the present description.
Figure 10A:
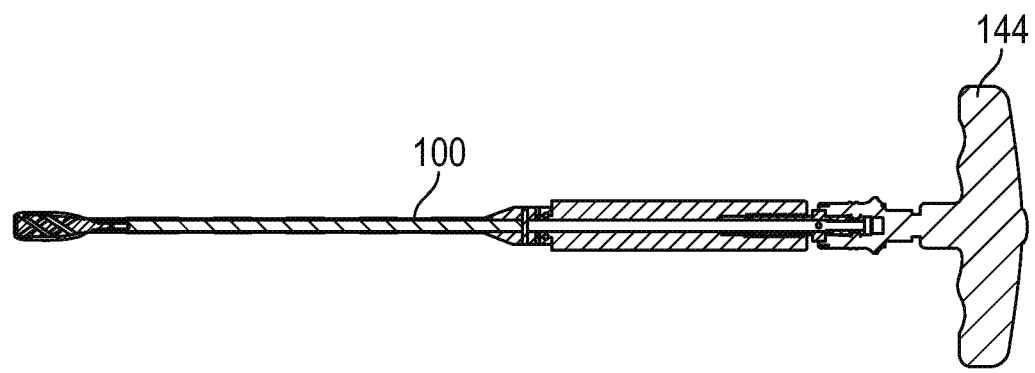
FIG. 10A provides a cross-sectional view an exemplary surgical distraction device according to the present description.
Figure 10B:
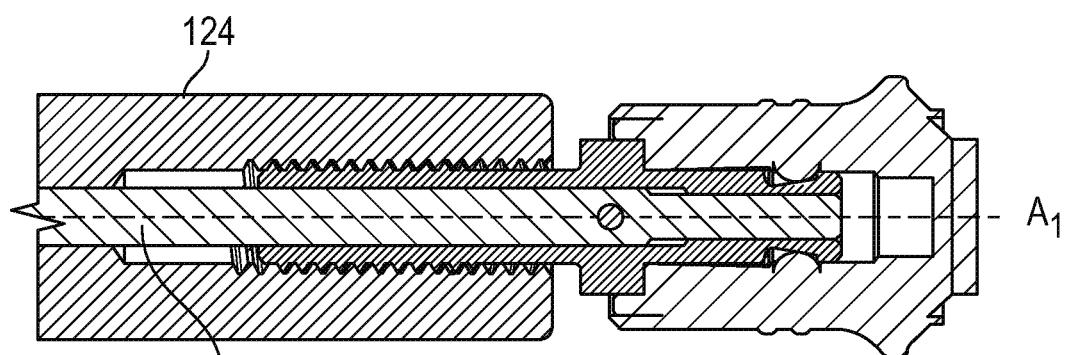
FIGS. 10B and 10C provide close up cross-sectional views of the surgical distraction device of FIG. 9A in two stages.
Figure 10C:
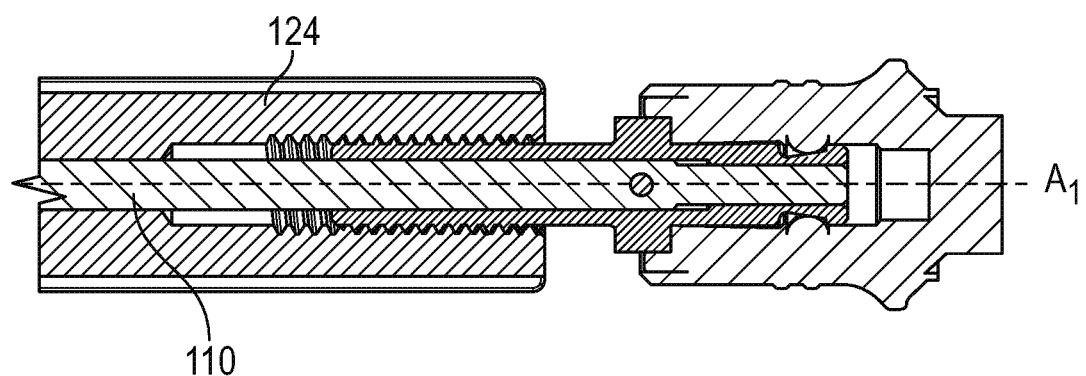

The turning nut 124 can facilitate translation of the housing 140 relative to the proximal drive assembly 110. The turning nut 124 can be coupled to the housing 140 via two pins 156, as shown in FIG. 9. These pins 156 can couple the turning nut 124 and the housing 140 in the longitudinal axis but still allow for the nut 124 to be rotated relative to the housing 140. When a user grasps to the turning handle 144 and begins rotating the turning nut 124, the turning nut 124 travels along the longitudinal axis $A_1$ of the proximal drive assembly and pushes/pulls the housing 140 along with it, thus expanding/contracting the paddles 114, 118 without rotating the housing 140. FIG. 10A shows a cross-sectional view of the surgical distraction device 100, and FIGS. 10B and 10C provide close-up cross-sectional views of the turning nut 124 at two different positions along the longitudinal axis $A_1$ of the proximal drive assembly 110. Alternatively, if a user holds on to the turning nut 124 and begins rotating the turning handle 144, the distal end of the surgical distraction device does rotate while simultaneously expanding/contracting the paddles 114, 118.

The surgical distraction devices 100 described herein can be used to determine the distance between adjacent vertebrae. For example, the surgical distraction device 100 can be inserted between two vertebrae of a patient, among other surgical uses. In one example, the surgical distraction device 100 can be rotated after insertion into the intervertebral space (i.e. the space between the two adjacent vertebrae) in order to facilitate determination of the distance across the intervertebral space, as further described below.

Figure 11C:
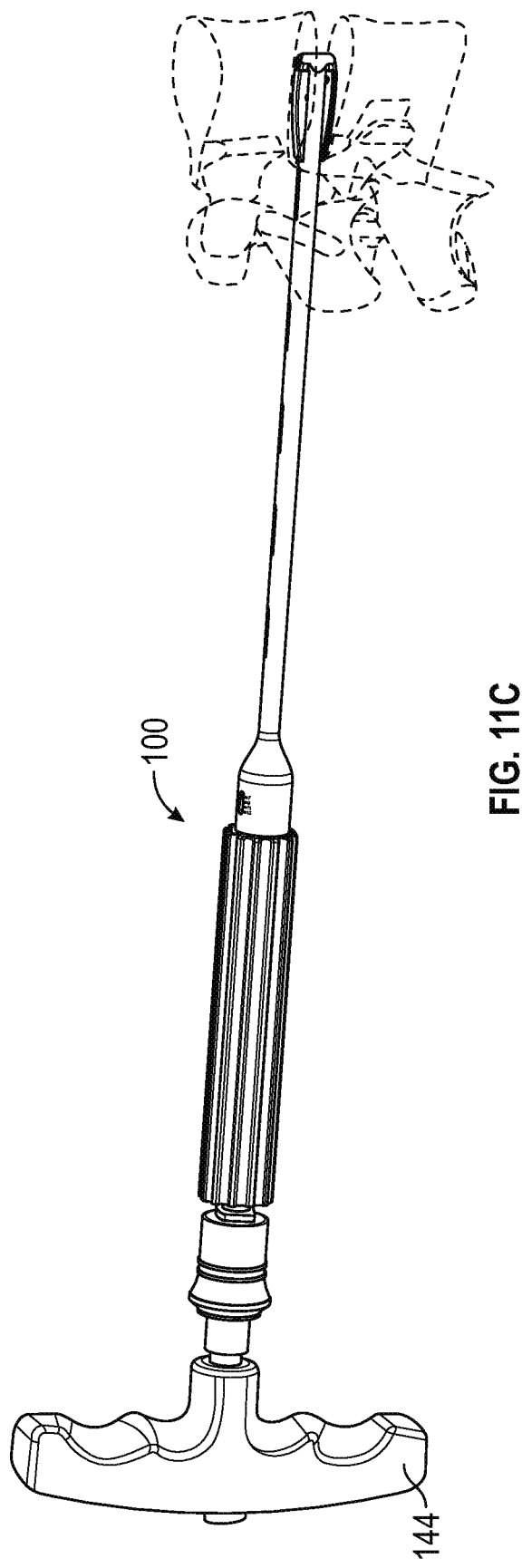
Figure 11D:
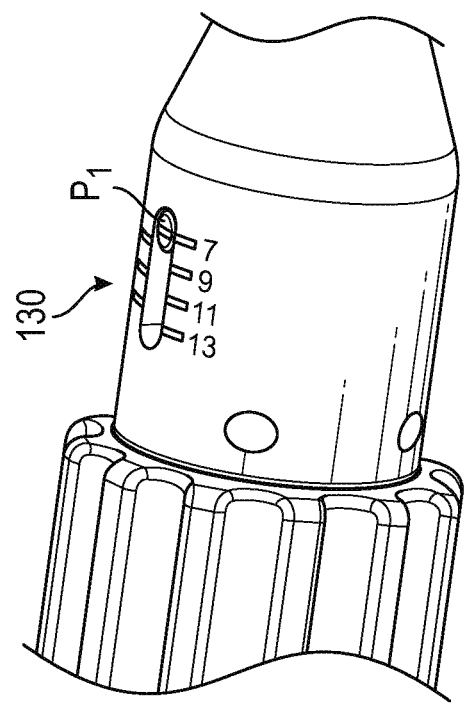
Figure 11E:
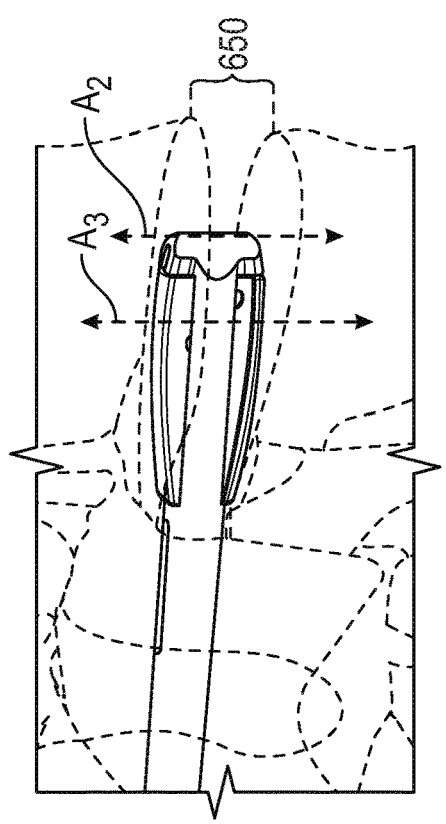
Figure 11F:
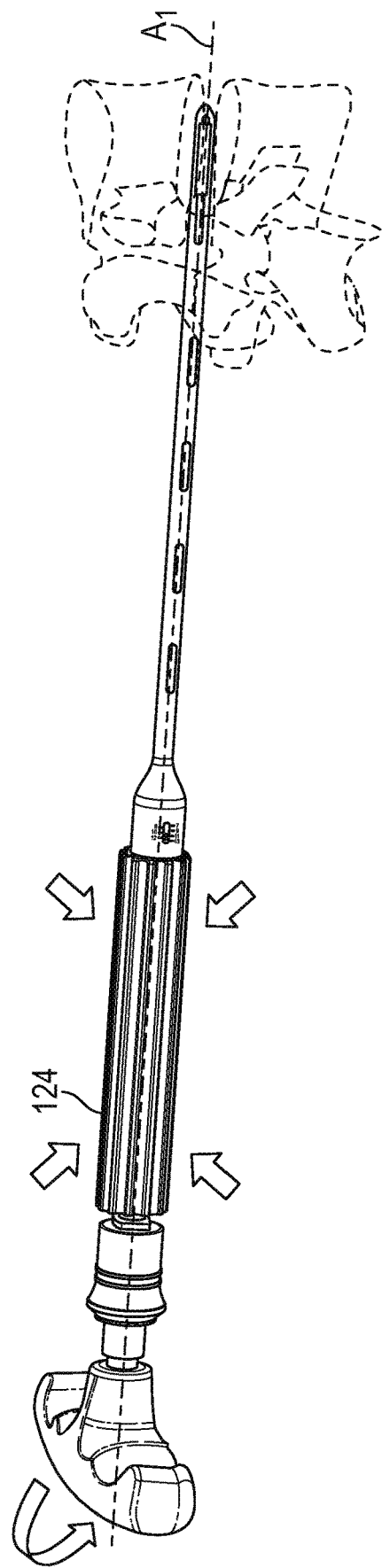
Figure 11G:
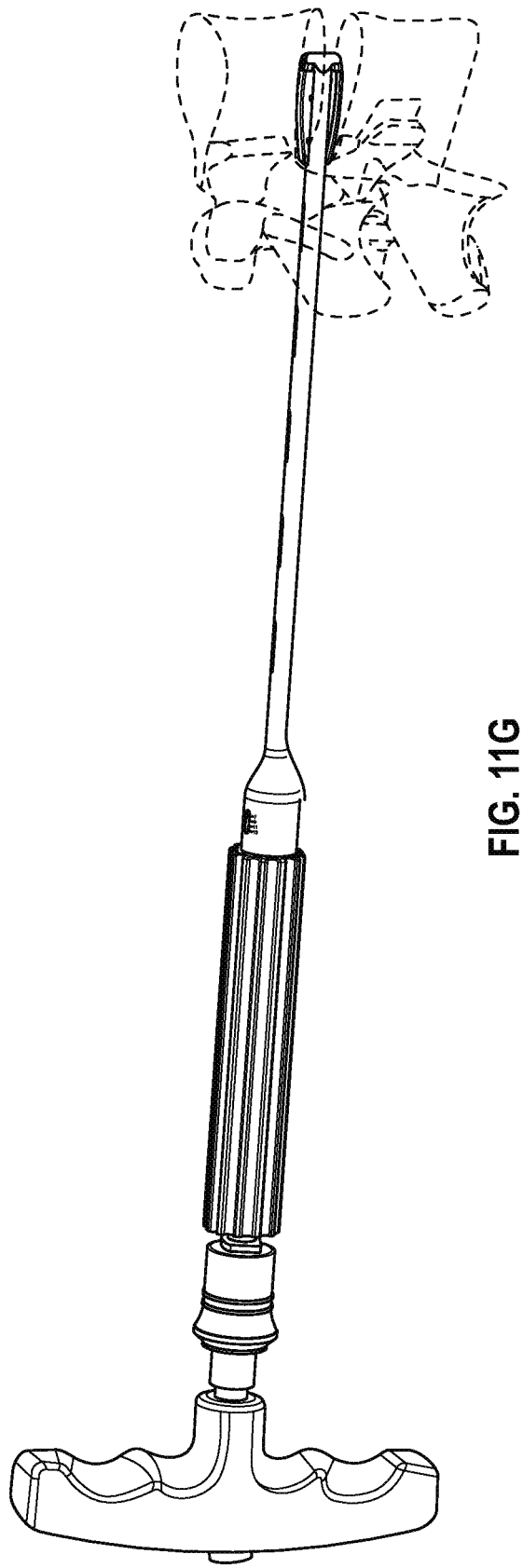
Figure 11H:
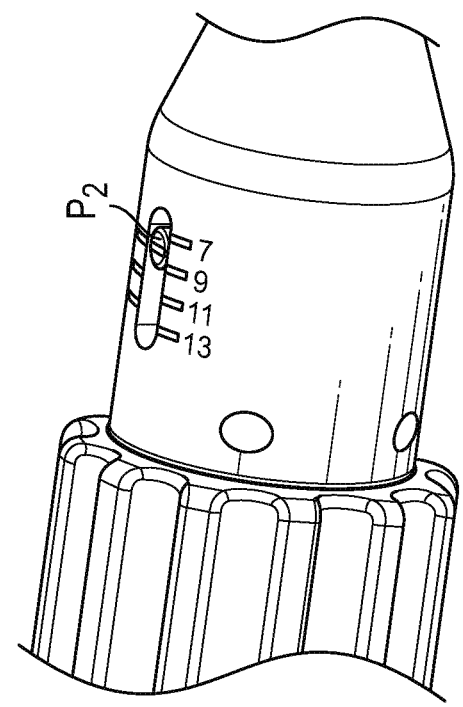
Figure 11I:
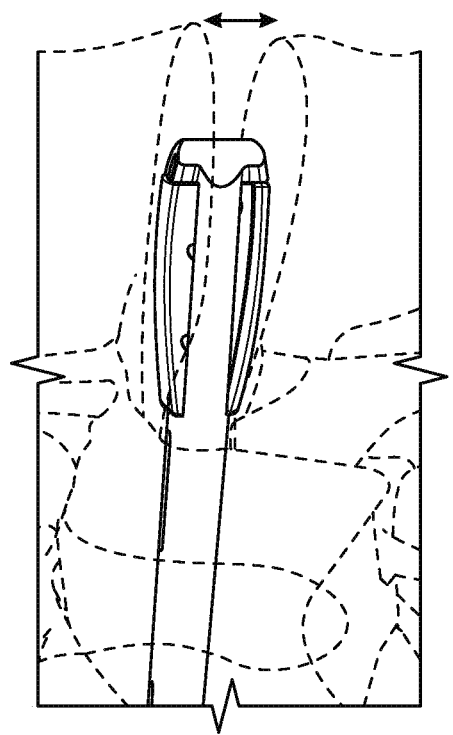

FIGS. 11A-11I illustrate one method of determining a space between two adjacent vertebrae according to one example. As shown in FIGS. 11A and 11B, the method can comprise inserting a distal end 142 of a distractor 100 into an intervertebral space 650. The distractor 100 of the methods described herein can generally relate to the distracters described in the previous figures, and thus any element numbers not specifically shown in the figures reference those provided in the foregoing figures. Next, the method can comprise attempting to rotate the distal end 142 of the distractor 100 to approximately ninety degrees such that an axis though a greatest width of the distal end ($A_2$) is aligned with the axis of the spine ($A_3$) (see FIG. 11E). As shown in FIG. 11D, the size indicator 130 may be in a first position $P_1$ that illustrates the size of implant that corresponds to the width across the paddles 114, 118, where at size $P_1$ the paddles have not been expanded outward from the pusher plate 108. The distal end 142 of the distractor 100 can be manipulated by the turning handle 144 at the proximal end 146 of distractor 100 which is coupled to the quick connect device 150. As shown in FIG. 11F, next the distractor 100 can be returned to its original orientation, likely where the paddle is in a substantially horizontal position within the intervertebral space 650. Additionally, the proximal drive assembly 110 can be actuated such that the first and second paddles 114, 118 translate away from a longitudinal axis $A_1$ of the proximal drive assembly 110 by engaging the turning nut 124 in place and rotating the turning handle 144. Next, as shown in FIGS. 11G, 11H and 11I, after expanding the paddles a certain distance, the operator can attempt, a second time, to turn the distal end 142 of distractor 100 ninety degrees such that axis $A_2$ is aligned with spinal axis $A_3$. Once again, the indicator 130 may be read to indicate the size of intervertebral implant that corresponds to a current distance across the width of the distractor, here shown by position $P_2$ on the indicator. This process can be repeated until the maximum diameter of the distal end 142 of the distractor 100 is capable of fitting snugly within the intervertebral space 650 when in an upright configuration (i.e. where the greatest width of the distractor aligned with the longitudinal axis of the spine). In the case where the distal end 142 of the distractor 100 is turned but incapable of fully rotating to 90 degrees to alignment with the spinal axis $A_3$, the surgeon will understand that the implant size corresponding to the most previous attempt to rotate the distractor will be the largest implant that can suitably fit in the intervertebral space.

Figure 12A:
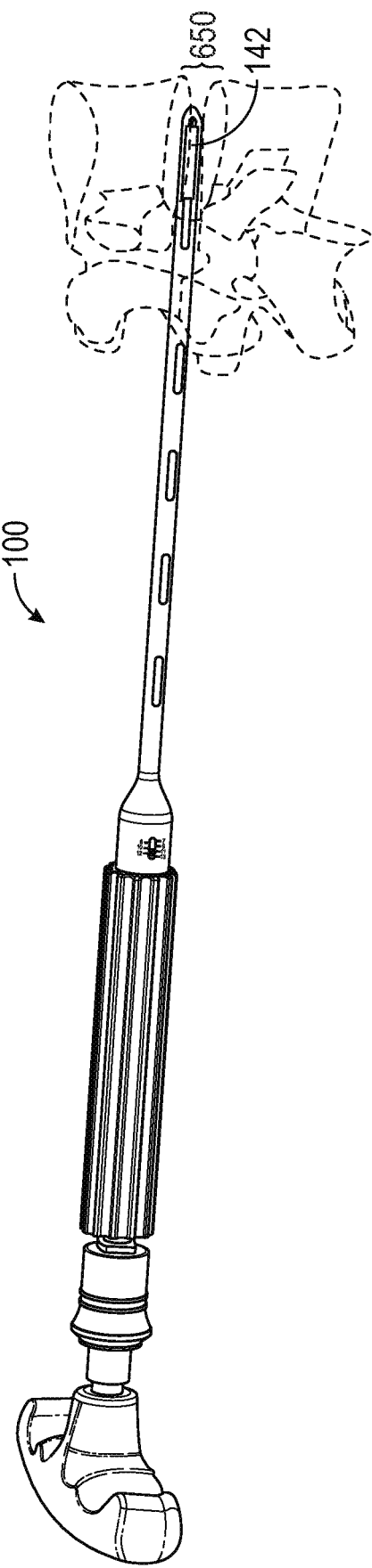
Figure 12B:
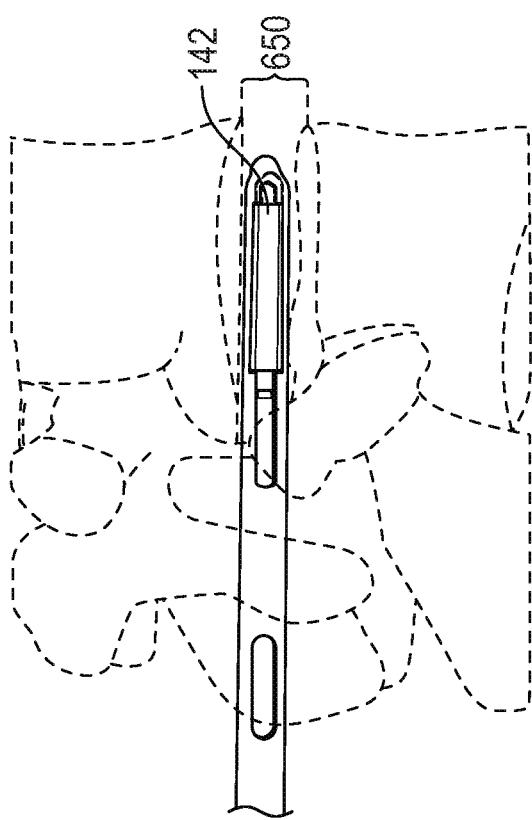
Figure 12C:
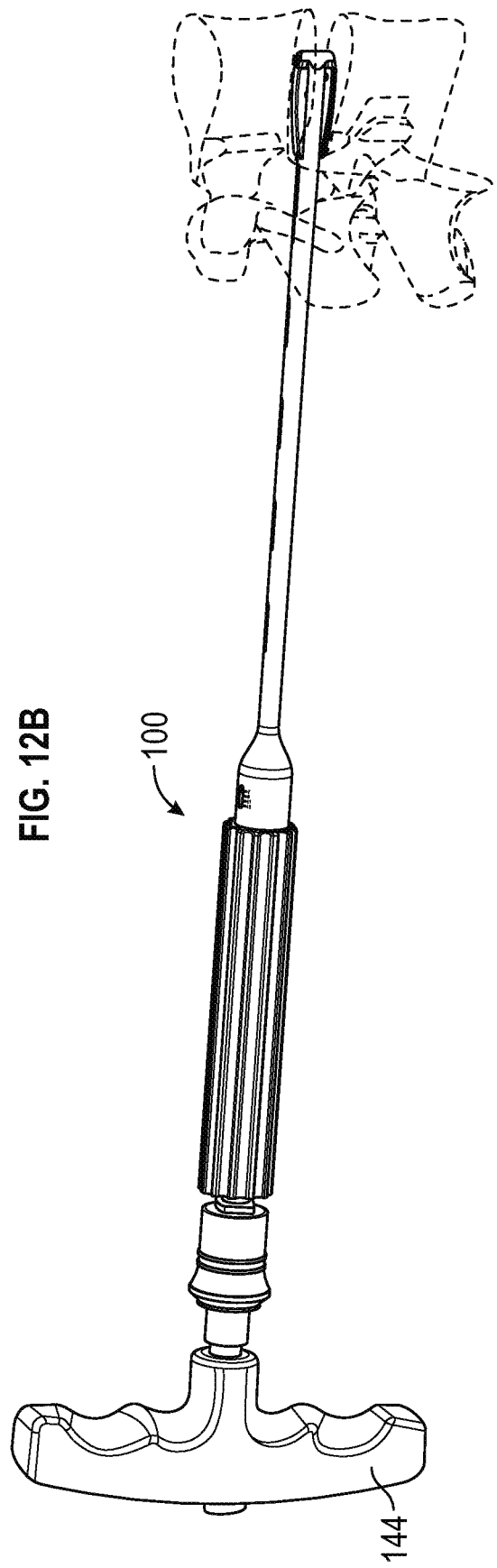
Figure 12D:
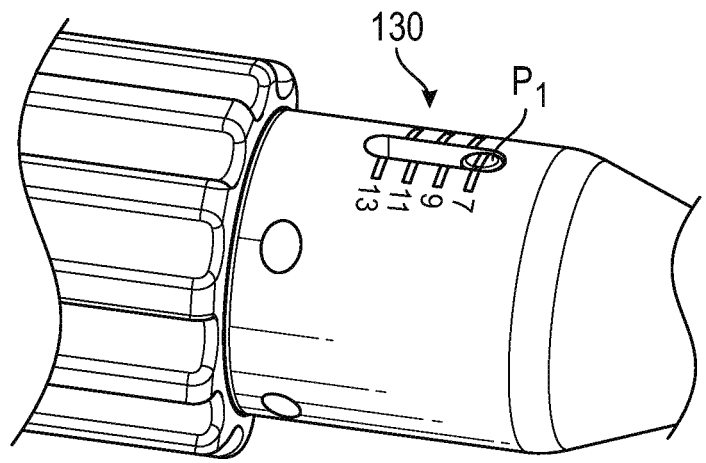
Figure 12E:
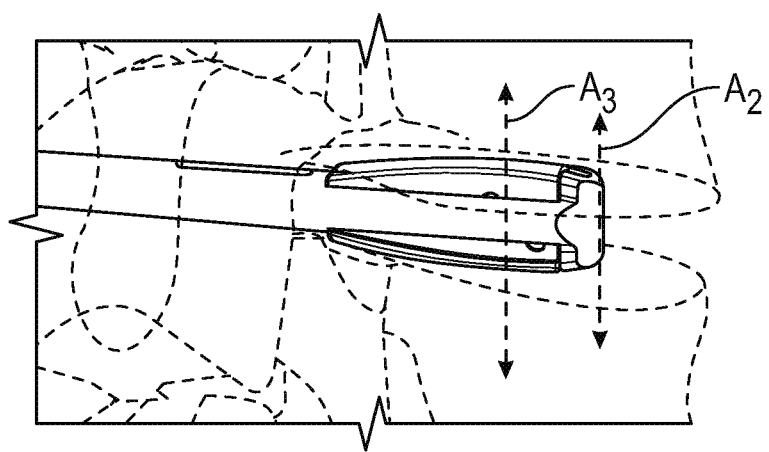
Figure 12H:
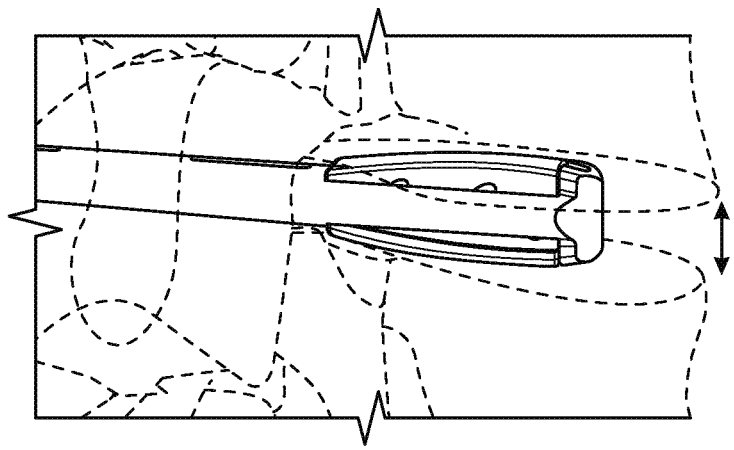
Figure 12I:
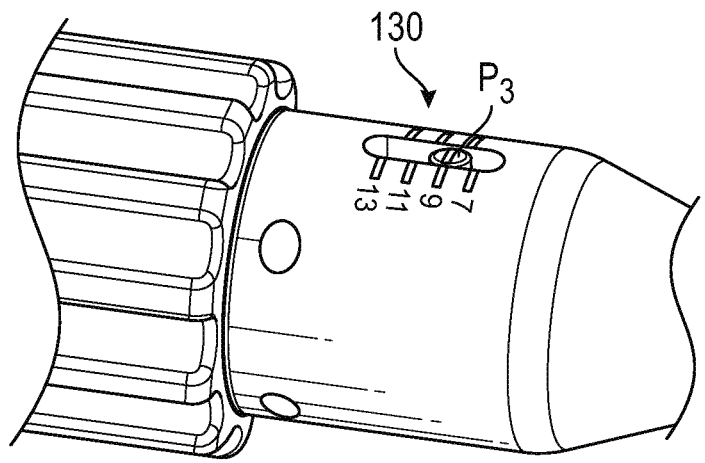
Figure 12J:
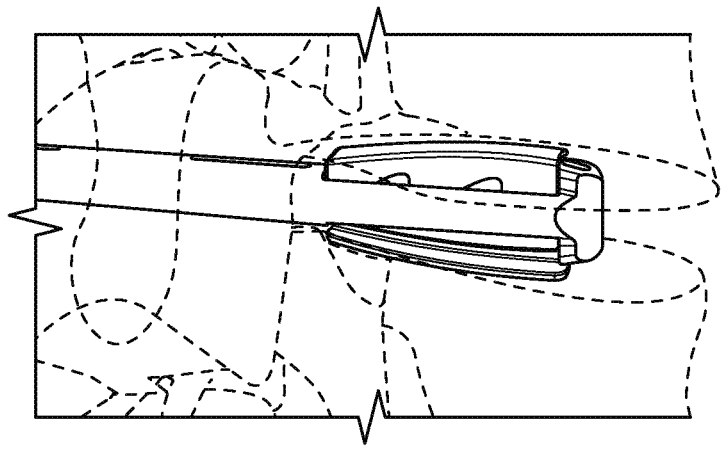

Another exemplary method of use is provided in FIGS. 12A-12G. The method can comprise inserting a distal end 142 of a distractor 100 into an intervertebral space 650, as shown in FIGS. 12A and 12B. Next, the operator can attempt to rotate the distal end 142 of the distractor 100 ninety degrees such that an axis through a greatest width of the distal end $A_2$ is aligned with the axis of the spine $A_3$ (as illustrated in FIGS. 12C, 12D and 12E), potentially using handle 144. The operator can then engage a proximal drive assembly 110 of the distractor 100 to cause the paddles to expand from a longitudinal axis of the proximal drive assembly 110 until the first and second engagement plates 123, 127 of the first and second paddles 114, 118 contact the first and second vertebrae bounding the intervertebral space. The mechanism of expanding the paddles is shown in FIG. 12F. Once the paddles 114 and 118 have encountered resistance against the surfaces of the adjacent vertebrae, the width of the distractor 100 can be determined using the size indicator 130. FIGS. 12G and 12H, and 12I and 12J, show the indicator at varying sizes including at position P2, which equates to an 8 mm implant, and position P3, which equates to a 9 mm implant. The width of the distractor in the plane in which the first and second paddles are translated after the paddles contact the first and second vertebra is equivalent to the distance across the intervertebral space.

In either method of use, the size determination of the intervertebral space can be used to choose an appropriately sized intervertebral implant, which can subsequently be implanted into the intervertebral space.

VARIOUS NOTES & EXAMPLES

Example 1 is a device comprising: a distal movement assembly comprising a pusher plate and a proximal drive assembly coupled to a proximal end of the pusher plate, the pusher plate comprising a first slot disposed therein extending along a first axis and a second slot disposed therein extending along a second axis, wherein the first slot extends from a first side of the pusher plate towards an opposed second side of the pusher plate, wherein the second slot extends from a second side of the pusher plate towards the first side, wherein the first axis is oriented at an angle of between about 60 degrees and about 160 degrees with respect to the second axis; a first paddle comprising a first actuation plate and a first engagement plate substantially transverse to the first actuation plate, the first paddle further comprising a first engagement member coupled to the first actuation plate for movably coupling the first paddle to the pusher plate when engaged with the first slot; and a second paddle comprising a second actuation plate and a second engagement plate substantially transverse to the second actuation plate, the second paddle further comprising a second engagement member coupled to the second actuation plate for movably coupling the second paddle to the pusher plate when engaged with the second slot; wherein rotational activation of the proximal drive assembly causes proximal or distal movement of the pusher plate, causing the first engagement member to move relative to the first slot and the second engagement member to move relative to the second slot, thereby moving the first paddle and the second paddle in opposing directions, each of the opposing directions orthogonal to a longitudinal axis of the device.

In Example 2, the subject matter of Example 1 optionally includes wherein the first engagement member comprises a first pin coupled to and extending from the first actuation plate.

In Example 3, the subject matter of Example 2 optionally includes wherein the second engagement member comprises a second pin coupled to and extending from the second actuation plate.

In Example 4, the subject matter of Example 3 optionally includes a housing that fully surrounds the proximal drive assembly and partially surrounds the pusher plate and first and second paddles.

In Example 5, the subject matter of Example 4 optionally includes wherein a first interior side of the housing has a first housing slot disposed therein that extends toward to the first exterior side of the housing that extends along the first axis of the first slot of the pusher plate, wherein a second interior side of the housing has a second housing slot disposed therein that extends toward to the second exterior side of the housing that extends along the second axis of the second slot of the pusher plate, wherein the first pin is movably coupleable to the first housing slot and the second pin is movable coupleable to the second housing slot.

In Example 6, the subject matter of any one or more of Examples 1-5 optionally include wherein the first engagement member comprises a first rail extending along at least a portion of the first actuation plate along the first axis of the first slot of the pusher plate, wherein the first rail and the first slot are matingly keyed.

In Example 7, the subject matter of Example 6 optionally includes wherein the second engagement member comprises a second rail extending along at least a portion of the second actuation plate along the second axis of the second slot of the pusher plate, wherein the second rail and the second slot are matingly keyed.

In Example 8, the subject matter of Example 7 optionally includes a housing that fully surrounds the proximal drive assembly and partially surrounds the pusher plate and first and second paddles.

In Example 9, the subject matter of any one or more of Examples 1-8 optionally include wherein the first slot comprises a first plurality of slots and wherein the first engagement member comprises a corresponding plurality of first engagement members.

In Example 10, the subject matter of Example 9 optionally includes wherein the second slot comprises a second plurality of slots and wherein the second engagement member comprises a corresponding plurality of second engagement members.

In Example 11, the subject matter of Example 10 optionally includes wherein first plurality of slots are parallel to one another and wherein the second plurality of slots are parallel to one another.

In Example 12, the subject matter of any one or more of Examples 1-11 optionally include wherein the pusher plate is threadably coupleable to the proximal drive assembly.

In Example 13, the subject matter of Example 12 optionally includes a turning nut coupled to the proximal drive assembly, wherein turning of the turning nut results in proximal or distal movement of the pusher plate.

In Example 14, the subject matter of Example 13 optionally includes wherein the turning nut is threadably engageable with the proximal drive assembly.

In Example 15, the subject matter of any one or more of Examples 1-14 optionally include an indicator that displays an implant size corresponding to the distance from an outer surface of the first engagement plate to an outer surface of the second engagement plate.

In Example 16, the subject matter of any one or more of Examples 1-15 optionally include wherein a distal end of the device insertable between adjacent vertebrae.

In Example 17, the subject matter of Example 16 optionally includes wherein the device is actuable to determine the distance between adjacent vertebrae.

Example 18 is a device, comprising: a distal movement assembly comprising a pusher plate and a proximal drive assembly coupled to a proximal end of the pusher plate, the pusher plate comprising a first slot disposed therein extending along a first axis and a second slot disposed therein extending along a second axis, wherein the first slot extends from a first side of the pusher plate towards an opposed second side of the pusher plate, wherein the second slot extends from a second side of the pusher plate towards the first side, wherein the first axis is oriented at an angle of between about 60 degrees and about 160 degrees with respect to the second axis; a first paddle comprising a first actuation plate and a first engagement plate substantially transverse to the first actuation plate, the first paddle further comprising a first pin coupled to and extending from the first actuation plate for movably coupling the first paddle to the pusher plate when engaged with the first slot; and a second paddle comprising a second actuation plate and a second engagement plate substantially transverse to the second actuation plate, the second paddle further comprising a second pin coupled to and extending from the second actuation plate for movably coupling the second paddle to the pusher plate when engaged with the second slot; wherein rotational activation of the proximal drive assembly causes proximal or distal movement of the pusher plate, causing the first engagement member to move relative to the first slot and the second engagement member to move relative to the second slot, thereby moving the first paddle and the second paddle in opposing directions, each of the opposing directions orthogonal to a longitudinal axis of the device.

In Example 19, the subject matter of Example 18 optionally includes a housing that fully surrounds the proximal drive assembly and partially surrounds the pusher plate and first and second paddles, wherein a first interior side of the housing has a first housing slot disposed therein that extends toward to the first exterior side of the housing that extends along the first axis of the first slot of the pusher plate, wherein a second interior side of the housing has a second housing slot disposed therein that extends toward to the second exterior side of the housing that extends along the second axis of the second slot of the pusher plate, wherein the first pin is movably coupleable to the first housing slot and the second pin is movable coupleable to the second housing slot.

Example 20 is a device, comprising: a distal movement assembly comprising a pusher plate and a proximal drive assembly coupled to a proximal end of the pusher plate, the pusher plate comprising a first slot disposed therein extending along a first axis and a second slot disposed therein extending along a second axis, wherein the first slot extends from a first side of the pusher plate towards an opposed second side of the pusher plate, wherein the second slot extends from a second side of the pusher plate towards the first side, wherein the first axis is oriented at an angle of between about 60 degrees and about 60 degrees with respect to the second axis; a first paddle comprising a first actuation plate and a first engagement plate substantially transverse to the first actuation plate, the first paddle further comprising a first rail coupled to and extending along at least a portion of the first actuation plate along the first axis of the first slot of the pusher plate for movably coupling the first paddle to the pusher plate when engaged with the first slot; and a second paddle comprising a second actuation plate and a second engagement plate substantially transverse to the second actuation plate, the second paddle further comprising a second rail coupled to and extending along at least a portion of the second actuation plate along the second axis of the second slot of the pusher plate for movably coupling the second paddle to the pusher plate when engaged with the second slot; wherein rotational activation of the proximal drive assembly causes proximal or distal movement of the pusher plate, causing the first engagement member to move relative to the first slot and the second engagement member to move relative to the second slot, thereby moving the first paddle and the second paddle in opposing directions, each of the opposing directions orthogonal to a longitudinal axis of the device.

In Example 21, the subject matter of Example 20 optionally includes wherein the first rail and the first slot are matingly keyed and wherein the second rail and the second slot are matingly keyed.

Example 22 is a method of determining the size of an intervertebral space, comprising: inserting a distal end of a distractor into an intervertebral space; attempting to turn the distal end of the distractor 90 degrees such that an axis through a greatest width of the distal end is aligned with the axis of the spine; engaging a proximal drive assembly of the distractor to move a pusher plate of the distractor along a longitudinal axis of the distractor, wherein engagement members disposed on each of the first and second paddle of the distractor engage with slots disposed in the pusher plate to cause the paddles to translate away from a longitudinal axis of the proximal drive assembly; determining an implant size corresponding to the width of the distractor in the plane in which the first and second paddles are translated using an implant size indicator.

In Example 23, the subject matter of Example 22 optionally includes wherein the width of the distractor in the plane in which the first and second paddles are translated after the paddles contact the first and second vertebra is equivalent to the distance across the intervertebral space.

Example 24 is a method of determining the size of an intervertebral space, comprising: inserting a distal end of a distractor into an intervertebral space; attempting to turn the distal end of the distractor 90 degrees such that an axis through a greatest width of the distal end is aligned with the axis of the spine; returning the distractor to its original orientation; engaging a proximal drive assembly of the distractor to move a pusher plate of the distractor along a longitudinal axis of the distractor, wherein engagement members disposed on each of the first and second paddle of the distractor engage with slots disposed in the pusher plate to cause the paddles to translate away from a longitudinal axis of the proximal drive assembly; attempting, an additional time, to turn the distal end of the distractor 90 degrees such that an axis through a greatest width of the distal end is aligned with the axis of the spine; and repeating the method until the maximum diameter of the distal end of the distractor that is capable of fitting snugly within the intervertebral space in an upright configuration is determined.

In Example 25, the subject matter of Example 24 optionally includes retracting the first and second paddles in the event that the distractor cannot be rotated 90 degrees into an upright configuration by advancing the proximal drive assembly in the distal direction.

In Example 26, the subject matter of any one or more of Examples 24-25 optionally include determining an appropriately sized implant that corresponds to the width of the distractor in a plane in which the first and second paddles are translating using an implant size indicator.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A device, comprising:
   a distal movement assembly comprising a pusher plate and a proximal drive assembly coupled to a proximal end of the pusher plate, the pusher plate comprising a first slot disposed therein extending along a first axis and a second slot disposed therein extending along a second axis, wherein the first slot extends from a first side of the pusher plate towards an opposed second side of the pusher plate, wherein the second slot extends from a second side of the pusher plate towards the first side, wherein the first axis is oriented at an angle of between about 60 degrees and about 160 degrees with respect to the second axis;
   a first paddle comprising a first actuation plate, a first engagement plate substantially transverse to the first actuation plate, and a first engagement member coupled to the first actuation plate for movably coupling the first paddle to the pusher plate when engaged with the first slot; and
   a second paddle comprising a second actuation plate and a second engagement plate substantially transverse to the second actuation plate, the second paddle further comprising a second engagement member coupled to the second actuation plate for movably coupling the second paddle to the pusher plate when engaged with the second slot;
   wherein rotational activation of the proximal drive assembly causes proximal or distal movement of the pusher plate, causing the first engagement member to move relative to the first slot and the second engagement member to move relative to the second slot, thereby moving the first paddle and the second paddle in opposing directions, each of the opposing directions orthogonal to a longitudinal axis of the device.

2. The device of claim 1, wherein the first engagement member comprises a first pin coupled to and extending from the first actuation plate.

3. The device of claim 2, wherein the second engagement member comprises a second pin coupled to and extending from the second actuation plate.

4. The device of claim 3, further comprising a housing that fully surrounds the proximal drive assembly and partially surrounds the pusher plate and first and second paddles.

5. The device of claim 4, wherein a first interior side of the housing has a first housing slot disposed therein that extends toward to the first exterior side of the housing that extends along the first axis of the first slot of the pusher plate, wherein a second interior side of the housing has a second housing slot disposed therein that extends toward to the second exterior side of the housing that extends along the second axis of the second slot of the pusher plate, wherein the first pin is movably coupleable to the first housing slot and the second pin is movable coupleable to the second housing slot.

6. The device of claim 1, wherein the first engagement member comprises a first rail extending along at least a portion of the first actuation plate along the first axis of the first slot of the pusher plate, wherein the first rail and the first slot are matingly keyed.

7. The device of claim 6, wherein the second engagement member comprises a second rail extending along at least a portion of the second actuation plate along the second axis of the second slot of the pusher plate, wherein the second rail and the second slot are matingly keyed.

8. The device of claim 7, further comprising a housing that fully surrounds the proximal drive assembly and partially surrounds the pusher plate and first and second paddles.

9. The device of claim 1, wherein the first slot comprises a first plurality of slots and wherein the first engagement member comprises a corresponding plurality of first engagement members.

10. The device of claim 9, wherein the second slot comprises a second plurality of slots and wherein the second engagement member comprises a corresponding plurality of second engagement members.

11. The device of claim 10, wherein first plurality of slots are parallel to one another and wherein the second plurality of slots are parallel to one another.

12. The device of claim 1, wherein the pusher plate is threadably coupleable to the proximal drive assembly.

13. The device of claim 12, further comprising a turning nut coupled to the proximal drive assembly, wherein turning of the turning nut results in proximal or distal movement of the pusher plate.

14. The device of claim 13, wherein the turning nut is threadably engageable with the proximal drive assembly.

15. The device of claim 1, further comprising an indicator that displays an implant size corresponding to the distance from an outer surface of the first engagement plate to an outer surface of the second engagement plate.

16. The device of claim 1, wherein a distal end of the device insertable between adjacent vertebrae.

17. The device of claim 16, wherein the device is actuable to determine the distance between adjacent vertebrae.

18. A device, comprising:
   a distal movement assembly comprising a pusher plate and a proximal drive assembly coupled to a proximal end of the pusher plate, the pusher plate comprising a first slot disposed therein extending along a first axis and a second slot disposed therein extending along a second axis, wherein the first slot extends from a first side of the pusher plate towards an opposed second side of the pusher plate, wherein the second slot extends from a second side of the pusher plate towards the first side, wherein the first axis is oriented at an angle of between about 60 degrees and about 160 degrees with respect to the second axis;

a first paddle comprising a first actuation plate and a first engagement plate substantially transverse to the first actuation plate, the first paddle further comprising a first rail coupled to and extending along at least a portion of the first actuation plate along the first axis of the first slot of the pusher plate for movably coupling the first paddle to the pusher plate when engaged with the first slot; and a second paddle comprising a second actuation plate and a second engagement plate substantially transverse to the second actuation plate, the second paddle further comprising a second rail coupled to and extending along at least a portion of the second actuation plate along the second axis of the second slot of the pusher plate for movably coupling the second paddle to the pusher plate when engaged with the second slot;

wherein rotational activation of the proximal drive assembly causes proximal or distal movement of the pusher plate, causing the first engagement member to move relative to the first slot and the second engagement member to move relative to the second slot, thereby moving the first paddle and the second paddle in opposing directions, each of the opposing directions orthogonal to a longitudinal axis of the device.

* * * * *